(12) United States Patent
Wieland et al.

(10) Patent No.: US 9,220,534 B2
(45) Date of Patent: Dec. 29, 2015

(54) IMPLANTATION PIN KIT AND METHOD FOR IMPLANTING AN IMPLANTATION PIN

(75) Inventors: Manfred Wieland, Kiel (DE); Edgar Kaiser, Probsteierhagen (DE)

(73) Assignee: Stryker Trauma GmbH (DE)

( * ) Notice: Subject to any disclaimer, the term of this patent is extended or adjusted under 35 U.S.C. 154(b) by 386 days.

(21) Appl. No.: 13/123,108

(22) PCT Filed: Apr. 27, 2009

(86) PCT No.: PCT/EP2009/055029
§ 371 (c)(1),
(2), (4) Date: May 31, 2011

(87) PCT Pub. No.: WO2010/040573
PCT Pub. Date: Apr. 15, 2010

(65) Prior Publication Data
US 2011/0224739 A1 Sep. 15, 2011

(30) Foreign Application Priority Data
Oct. 10, 2008 (EP) .................................... 08017885

(51) Int. Cl.
*A61B 17/86* (2006.01)
*A61B 17/56* (2006.01)
(Continued)

(52) U.S. Cl.
CPC ................ *A61B 17/68* (2013.01); *A61B 17/88* (2013.01); *A61B 2017/00004* (2013.01)

(58) Field of Classification Search
CPC .... A61B 17/88; A61B 17/866; A61B 17/864; A61B 17/8625; A61B 17/86; A61B 17/68; A61B 2017/8655; A61B 2017/00004

USPC .............................. 606/92–95, 151, 300–331
See application file for complete search history.

(56) References Cited

U.S. PATENT DOCUMENTS 5,360,302 A 11/1994 MacMartin
5,649,937 A * 7/1997 Bito et al. ..................... 606/139
(Continued)

FOREIGN PATENT DOCUMENTS

JP 2007222752 A 9/2007
WO 2008/034276 A2 3/2008
(Continued)

OTHER PUBLICATIONS

International Search Report, PCT/EP2009/055029, dated Sep. 10, 2009.

*Primary Examiner* — Zade Coley
(74) *Attorney, Agent, or Firm* — Lerner, David, Littenberg, Krumholz & Mentlik, LLP

(57) ABSTRACT

An implantation pin kit and a method for implanting an implantation pin includes a cannulated implantation pin having a channel and a heating device. The channel of the pin extends in a longitudinal direction of the pin and connects a proximal opening at a proximal end of the pin with a distal opening at a distal end of the pin. The channel of the pin and the heating device are adapted such that the heating device can be accommodated within at least a portion of the channel of the pin. The heating device is adapted to thermally heat material comprised in at least one of the pin and the heating device. Thereby, meltable material of the pin can be liquefied or additional liquefied meltable material can be inserted into the pin and the liquefied material can then be push towards and out of the distal opening in order to augment and fix the implantation pin in a target structure.

4 Claims, 2 Drawing Sheets

(51) Int. Cl.
 *A61B 17/68* (2006.01)
 *A61B 17/88* (2006.01)
 *A61B 17/00* (2006.01)

(56) References Cited

U.S. PATENT DOCUMENTS

| | | | |
|---|---|---|---|
| 5,666,779 A | 9/1997 | Fuchs et al. | |
| 5,871,484 A | 2/1999 | Spievack et al. | |
| 5,993,458 A | 11/1999 | Vaitekunas et al. | |
| 6,080,161 A * | 6/2000 | Eaves et al. | 606/76 |
| 6,132,214 A | 10/2000 | Suhonen et al. | |
| 6,214,012 B1 | 4/2001 | Karpman et al. | |
| 6,332,885 B1 | 12/2001 | Martella | |
| 6,554,852 B1 * | 4/2003 | Oberlander | 606/232 |
| 6,565,572 B2 | 5/2003 | Chappius | |
| 6,623,487 B1 * | 9/2003 | Goshert | 606/329 |
| 6,918,766 B1 | 7/2005 | Hall et al. | |
| 6,921,264 B2 * | 7/2005 | Mayer et al. | 433/173 |
| 7,008,226 B2 * | 3/2006 | Mayer et al. | 433/173 |
| 7,087,073 B2 * | 8/2006 | Bonutti | 606/232 |
| 7,250,055 B1 | 7/2007 | Vanderwalle | |
| 7,255,713 B2 | 8/2007 | Malek | |
| 7,335,205 B2 * | 2/2008 | Aeschlimann et al. | 606/232 |
| 7,354,442 B2 | 4/2008 | Sasso et al. | |
| 7,429,266 B2 * | 9/2008 | Bonutti et al. | 606/232 |
| 7,510,397 B2 | 3/2009 | Hochman | |
| 7,608,062 B2 | 10/2009 | Sweeney | |
| 7,615,070 B2 | 11/2009 | Biscup | |
| 7,717,947 B1 * | 5/2010 | Wilberg et al. | 606/304 |
| 2003/0003128 A1 | 1/2003 | Chiarelli | |
| 2003/0220700 A1 * | 11/2003 | Hammer et al. | 623/23.58 |
| 2004/0030341 A1 | 2/2004 | Aeschlimann et al. | |
| 2004/0038180 A1 | 2/2004 | Mayer et al. | |
| 2004/0053196 A1 | 3/2004 | Mayer et al. | |
| 2005/0059972 A1 | 3/2005 | Biscup | |
| 2006/0105295 A1 | 5/2006 | Mayer et al. | |
| 2007/0260250 A1 * | 11/2007 | Wisnewski et al. | 606/73 |
| 2007/0270833 A1 * | 11/2007 | Bonutti et al. | 606/61 |
| 2008/0021474 A1 * | 1/2008 | Bonutti et al. | 606/64 |
| 2008/0125815 A1 | 5/2008 | Heaven et al. | |
| 2008/0262517 A1 * | 10/2008 | Wieland | 606/151 |

FOREIGN PATENT DOCUMENTS

| | | | | |
|---|---|---|---|---|
| WO | WO 2008034278 A1 * | 3/2008 | | F16B 13/06 |
| WO | 2008/116203 A2 | 9/2008 | | |

* cited by examiner

IMPLANTATION PIN KIT AND METHOD FOR IMPLANTING AN IMPLANTATION PIN

CROSS REFERENCE TO RELATED APPLICATIONS

The present application is a national phase entry under 35 U.S.C. §371 of International Application. No. PCT/EP2009/055029, filed Apr. 27, 2009, published in English, which claims the benefit of European Patent Application No. 08 017 885.8, filed Oct. 10, 2008, published as EP 2174607A. The disclosures of said applications are incorporated by reference herein.

FIELD OF THE INVENTION

The invention relates to an implantation pin kit including an implantation pin which might be fixed in a target structure such as a human bone. Furthermore, the invention relates to a method for implanting an implantation pin into such target structure.

TECHNICAL BACKGROUND

In the prior art, several implantation devices for humans or animals are known. The implants at least partly create positive-fit connections to human or animal tissue parts, particularly to skeletal parts such as bones. Therein, the implants may help to connect tissue parts together or they may help to connect tissue parts to other means supporting or replacing tissue parts or to other therapeutic auxiliary devices.

Known implants for creating connections to skeletal parts include screws, pins, staples, etc. for connecting one bone to another bone or for connecting a bone to artificial carrying, stabilizing or supporting parts or to parts replacing skeletal parts such as stabilization or fixation plates, wires, artificial joint elements, artificial teeth, bone grafts, etc. Such known implants may consist for example of metal or plastic or another material having bio-compatible characteristics as well as sufficient mechanical stability. After healing, the implant may be removed by a further operation or may be left in the body where it remains permanently or, in case that bio-resorbable material is used for the implant, is gradually decomposed and replaced by vital tissue.

It is known in the art to provide implantation pins comprising a material which can be liquefied by application of ultrasonic vibrations. Therein, an implantation pin comprises a mouldable material such as a thermoplastic polymer which, upon applying ultrasonic vibrations, may be liquefied and then flows into adjacent tissue, for example into pores of an adjacent bone material, in order to fix the implantation pin into the target structure. Such implantation pin is described in a commonly assigned co-pending European patent application no. 07008122.9, published as EP 1982662A, as well as in the commonly assigned co-pending PCT application no. PCT/EP2008/000789 and U.S. Patent Publication No. 2008/0262517.

However, conventional implantation pins in which ultrasonic energy is used in order to liquefy mouldable material may suffer from various problems which complicate their use in actual surgical operations and which furthermore increase the costs inherent therewith.

SUMMARY OF THE INVENTION

The inventors of the present application have remarked that, in implanting conventional implantation pins, the application of ultrasonic energy may require that a substantial pressure is applied to the implantation pin during an actual surgical operation for transmitting ultrasonic vibrations to the implantation pin in order to liquefy its mouldable material. The application of such substantial pressure may be undesired as the tissue into which the implantation pin is to be implanted may be very sensitive to such pressure. Furthermore, the application of ultrasonic vibrations may necessitate a complicated and costly ultrasonic sonotrode.

Accordingly, there may be a need for an implantation pin which allows to overcome at least some of the problems inherent with conventional implantation pins and for a method to implant such implantation pins. Particularly, there may be a need for an implantation pin which can be implanted without applying significant pressure to the pin. Furthermore, there may be a need for an implantation pin which can be produced and implanted at low costs.

These needs may be met by an implantation pin kit and a method for implanting an implantation pin according to the independent claims of the present application. Advantageous embodiments of the invention are described with respect to the dependent claims.

According to a first aspect of the present invention, an implantation pin kit is proposed. Therein, the implantation pin kit comprises a cannulated implantation pin having a channel and a heating device. The channel of the pin extends in a longitudinal direction of the pin and connects a proximal opening at a proximal end of the pin with a distal opening at a distal end of the pin. The channel of the pin is adapted to accommodate the heating device. The heating device is adapted to be accommodated within at least a portion of the channel of the pin and is furthermore adapted to thermally heat material comprised in the pin and/or the heating device.

It may be seen as the gist of the present invention that, in implanting an implantation pin, instead of applying ultrasonic vibrations in order to liquefy a mouldable material for augmenting and fixing the pin, thermal energy may be used to melt a meltable material which then may flow through a channel in the cannulated implantation pin towards an outlet, namely a distal opening at a distal end of the pin, to thereby augment and fix the pin in neighbouring tissue. By replacing the application of ultrasonic vibration energy by the supply of thermal energy in order to liquefy meltable material, it is not necessary anymore to apply a significant pressure to the implantation pin when fixing it in a target structure. Furthermore, there may be no need for a complicated and expensive ultrasonic sonotrode. Instead, the energy necessary for liquefying the meltable material may be provided by a simple heating device such as for example a heating wire.

Depending on the respective embodiment, which will be described in detail further below, the application of thermal energy may be either used for melting meltable material of the pin itself wherein the melted material subsequently may have to be forced out of the distal opening by applying mechanical pressure. Or the thermal energy may be used to preheat a region adjacent to the pin's channel such that meltable material which is melted externally to the pin may be provided to the pin's channel and may flow through the preheated channel without solidifying before reaching the distal opening of the channel.

In the following, further possible features, embodiments and advantages of the present invention are described in detail.

The implantation pin kit comprises at least two components, namely the cannulated implantation pin and the heating device. Optionally, the implantation pin kit may comprise further components such as for example an additional holding device for grasping the pin and holding it in position during implantation, a plunger for pressing melted material towards an outlet at the distal opening of the shaft and/or a melted material supply device for supplying melted material to be inserted into the pin.

The heating device may be adapted such that, when energy such as e.g. electrical energy is supplied to the heating device, this energy is converted into heat which heat may then be transferred to adjacent material. For this purpose, the geometry of the heating device may be chosen such that, when inserted into the pin's channel, the heating device comes into close mechanical contact to the walls of the channel in order to transfer heat to the material of these walls.

The proximal opening arranged at a proximal end of the implantation pin may be adapted and arranged such that the heating device may be inserted into and withdrawn from the channel during an implantation procedure. The distal opening of the channel may be positioned at a surface normal to the pin's longitudinal axis at a distal end of the pin. In this way, melted material produced within the channel or externally supplied to the channel may be pushed through the channel and exit the channel at a distal outlet thereby bringing the melted material to a position deep inside the target structure. Alternatively, the distal opening of the channel may be positioned at a lateral surface of the pin's shaft. In this way, the liquefied meltable material may be transferred to a circumferential surface of the shaft such that a positive fit between the lateral surface of the pin's shaft and the side walls of a recess in the target structure may be obtained. In a further alternative, the channel discharges into a plurality of distal openings at various surface portions, preferably at opposing lateral surface portions, of the shaft. In other words the channel may branch off in several sub-channels which may lead to a plurality of discharge openings. These discharge openings may be positioned at the lateral surface of the shaft at opposing locations such that the liquefied meltable material may be distributed homogeneously around the lateral surfaces of the pin's shaft.

According to an embodiment of the present invention, the heating device comprises a heating wire adapted to be thermally heated upon application of an electrical current. Using such heating wire the heating device may be implemented in a very simple and cheap way. The heating wire may have a circular cross section which fits into the channel of the pin. Preferably, the heating wire comprises a closed loop such that, when the heating wire is inserted into the pin's channel, both ends of the heating wire may be arranged adjacent to the proximal opening of the channel. For example, the heating wire may be implemented using a coaxial cable wherein the inner and the outer conductor are connected at a distal end of the cable and an electric voltage may be applied at the proximal ends. The source of electrical energy may be integrated into the heating device or, alternative, may be provided by an external device.

According to an embodiment of the present invention, material of the pin adjacent to the channel is adapted to be thermally melted and the heating device is adapted to thermally heat material of the pin adjacent to the channel in order to melt it. In such embodiment, meltable material may be produced directly inside the pin using the heating device inserted into the pin's channel. The melted material may then flow or be pushed out of the distal opening and into the adjacent target structure and, upon resolidification, may fixe the pin in the target structure. No additional melted material has to be provided from externally. Accordingly, the pin may be easily handled as all necessary meltable material is already provided within the pin.

Herein, the term "meltable" may be understood in a way that the material may be melted at relatively low temperatures, e.g. below 300° C., preferably below 200° C. and more preferable below 130° C. In other words, the material may be meltable at temperatures which may be easily attained using the respective heating device.

The implantation pin may consist entirely of one single material. Accordingly, the entire implantation pin may be made from a meltable material and can be fabricated for example as a single integral component. Providing the entire implantation pin with only one material may significantly simplify the fabrication of such pin. For example, the pin may be made by injection moulding. Alternatively, the pin may comprise different materials wherein an inner material in a region adjacent to the pin's channel is meltable at relatively low temperatures whereas an outer material is not meltable or only meltable at substantially higher temperatures thereby providing a non-meltable protection sleeve.

The meltable material may be any material which can be liquefied by application of thermal energy. In other words, the meltable material should be such that it is originally solid and becomes liquid or plastified upon application of thermal energy and, upon subsequently cooling down, may resolidify again. Preferably, the meltable material may be adapted in such a way that its liquefaction may be achievable by an energy input which does not destroy or harm human tissue, particularly bone tissue. The meltable material can be for example a thermoplastic material. Such material can liquefy or plastify at elevated temperatures. For example, the material and the geometry of the implantation pin may be chosen such as to exhibit a sufficient degree of liquefaction at temperatures below a predetermined temperature threshold such as not to substantially harm any tissue.

Examples of meltable or mouldable materials may be thermoplastics such as e.g. PA (Polyamide), PC (Polycarbonate), PP (Polypropylene), PE (Polyethylene), PMMA (Polymethylmethacrylate), POM (Polyoxymethylene), PES (Polyethersulfone), PEI (Polyetherimide), PPSU (Polyphenylsulphone), PEEK (Polyetheretherketone), PSU (Polysulfone) or the bio-compatible or bio-resorbable materials mentioned further below.

Optionally, at least one of a surface coating of the implantation pin, a bulk material of the implantation pin and the meltable material comprises a bio-compatible material. A bio-compatible material may be a material which does not negatively interfere with human or animal tissue. Examples of bio-compatible materials may be specially adapted metal alloys such as titanium or specific plastics, e.g. PEEK (Polyetheretherketone), UHMWPE (Ultra high molecular weight polyethylene), PLA (Polylactic acid), PLLA (Poly-L-lactide), PLDLA (Poly(D,L-Lactid)), PDLLA (Poly-DL-lactide), PVDF (Polyvinylidene Difluoride). Such bio-compatible materials may be used especially for the outer "skin" of the implantation pin in order to avoid rejection of the implantation pin when implanting the pin for example into a bone. It is advantageous to use a bio-compatible thermoplastics which can be used both for the outer skin of the pin as well as for the inner mouldable material such that the entire implantation pin can be made of this single bio-compatible material.

Further optionally, at least one of a surface coating of the implantation pin, a bulk material of the implantation pin and the mouldable material comprises a bio-absorbable material. Such bio-absorbable material may be absorbed by a human or animal's body after a certain period such that parts of the pin consisting of such bio-absorbable material may be replaced by living tissue after this period, thereby providing an increased stability of the connection between implantation pin and living tissue and reducing rejection reactions.

One possible bio-absorbable material comprises a copolymer comprising between 50% and 90% Poly-L-lactide and between 10% and 50% Poly-D, L-lactide. In particular, the bio-absorbable material may be a copolymer comprising 70 weight % Poly-L-lactide and 30 weigh % Poly-D, L-lactide. Preferably, the bio-absorbable material may be formed as an amorphous material.

The above described material may be a suitable material for an implantation pin, which material may exhibit a suitable tensile strength of about 60 MPa, and a suitable E-modulus of about 3500 MPa. Furthermore, an implantation pin including the above material may retain its strength for about a sufficient time when implanted into a human or animal body. Such a time span may be about 16 to 26 weeks. The described copolymer may have a resorption time of about two to three years in a human or animal body. The material may further exhibit an increase of implant volume up to 200% after 24 month from the implantation in the target structure. Such a material may further be easily to be sterilized by y-radiation. A suitable energy dose may be between 20 kGy and 30 kGy, in particular below 25 kGy.

The liquefaction of the meltable material should be such that the liquefied material can easily flow through the pin's channel. Accordingly, the liquefied material should have such low viscosity that it can be pushed through the channel without applying excessive pressure onto the implantation pin in order not to damage or harm the target bone structure.

According to a further embodiment of the present invention, the implantation pin kit further comprises a plunger. The plunger is adapted to press melted material which has been previously generated adjacent to the channel towards the distal opening of the pin. The plunger may have a geometry adapted to the cross section of the melted region adjacent to the pin's channel. Accordingly, the plunger may be pushed into the pin thereby pressing the previously melted material towards the opposite end of the pin where it may exit through the distal opening and into the adjacent target structure. Thus, even when the melted material has a high viscosity such that it may not easily flow out of the pin, it may be forced out of the pin using the plunger. Furthermore, the melted material may be pushed with elevated pressure out of the distal opening and into the adjacent target material structure. Thereby, the melted material may be pressed e.g. deep into pores of a bone into which the pin is to be implanted.

According to a further embodiment of the present invention, the implantation pin kit further comprises a melted material supply device for supplying melted material to the proximal opening of the channel of the pin. The melted material supply device may be an external device in which meltable material may be heated until it melts and may then be pressed into the proximal opening of the channel of the pin. Such external device may be mechanically coupled the pin's head during an implantation procedure. In such implementation, it may be advantageous that the pin's channel may be preheated using the heating device such that the externally supplied melted material need not to be introduced into a cold channel with the risk of fast resolidification thereby clogging the channel. Alternatively, the melted material supply device may be integrated into the heating device wherein the heating device may be used to heat and melt additional material which may then be supplied to the pin's channel.

According to a further embodiment of the present invention, in the implantation pin kit, the heating device is provided as an insert wherein the insert comprises a meltable material adjacent to a heating wire and wherein the insert further comprises a compression arrangement adapted to press melted material out of the insert and towards the distal opening of the channel of the pin. The entire insert may have a geometry such that it may be fitted into the pin's channel. When the insert is in the channel at a position adjacent to the distal opening, heat may be generated by the heating wire and may be transferred to the meltable material. When melted, the material may be pressed out of the insert using the compression arrangement and into the pin where it may exit through the distal openings into the adjacent target structure. Such procedure may also be referred as "retro-welding".

According to a second aspect of the present invention, a method for implanting an implantation pin using an implantation pin kit as described above is proposed. The method comprises the following steps: inserting the implantation pin into a target structure; accommodating the heating device within the channel of the pin; heating material adjacent to the channel of the pin using the heating device; melting of meltable material within the pin using the heating device; and pressing the melted material out of the distal opening of the channel of the pin.

It has to be noted that embodiments of the invention are described with reference to different subject matters. In particular, some embodiments are described with reference to apparatus type claims whereas other embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

The aspects and embodiments defined above and further aspects and embodiments of the present invention are apparent from the examples of embodiments to be described hereinafter and are explained with reference to the examples of embodiment. The invention will be described in more detail hereinafter with reference to examples of embodiment but to which the invention is not limited.

BRIEF DESCRIPTION OF THE DRAWINGS

It is to be noted that the figures are only schematic and not to scale. Corresponding reference signs have been used throughout the figures to designate similar elements.

DETAILED DESCRIPTION OF PREFERRED EMBODIMENTS

Figure 1:
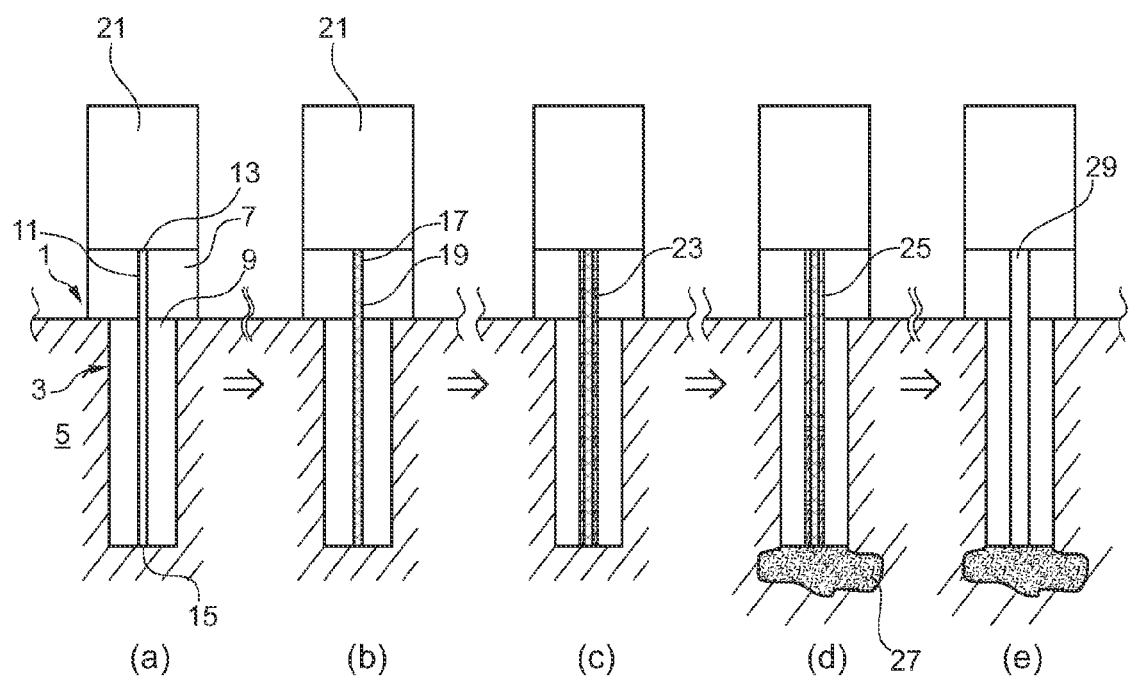
FIG. 1 shows an implantation pin kit and a sequence of its use during an implantation method according to a first embodiment of the present application.

In FIG. 1, a sequence of a method for implanting an implantation pin 1 according to an embodiment of the present invention is schematically shown in its sequence steps.

In a step (a), the implantation pin 1 is inserted into a recess 3 which has been previously prepared in a target structure 5 such as a human bone. The pin 1 comprises a pin head 7 and a pin shaft 9. The pin head 7 has a larger cross section than the pin shaft 9. The cross section of the pin shaft 9 is selected such as to be slightly smaller than the cross section of the recess 3. Accordingly, the pin 1 can be easily inserted into the recess 3 until its pin head 7 abuts to the circumference of the recess 3.

The implantation pin 1 comprises a channel 11 which extends along a longitudinal direction of the pin 1 from a proximal opening 13 at a proximal end at an upper side of the pin head 7 to a distal opening 15 at the lower side of the pin shaft 9. The material of the pin head comprises a meltable, preferably bio-compatible material.

In step (b), a heating wire 17 which may serve as a heating device 19 is inserted into the pin's channel 11. The heating wire 17 is introduced into the channel at the proximal opening 13 and is pushed through the channel 13 until it reaches a region close to the distal opening 15. The geometry of the heating wire is chosen such that, when introduced into the pin's channel, it comes into mechanical and thermal contact to the pin's material.

The heating wire 17 is introduced into the channel 11 using an implantation device 21. The implantation device 21, which is shown only very schematically, may at the same time serve for holding the implantation pin, pushing the heating wire 17 into the channel 11 and supplying electrical energy to the heating wire 17 in order to heat same to a temperature which is sufficiently high for melting the meltable material adjacent to the channel 11.

In step (c), the meltable material 23 adjacent to the channel 11 is melted upon application of electrical energy to the heating wire 17.

In step (d), the previously melted material 23 is then pushed towards the distal opening 15 using a plunger 25. The plunger 25 may be operated and pushed by the implanting device 21 or by a separate device and may have a cross section which approximately corresponds to the extension of the previously melted region 23. By pushing the plunger 25 towards the distal opening 15, the previously melted material is pushed out of the distal opening 15 where, upon subsequent resolidification, it serves for augmenting and fixing the pin 1 within the recess 3 of the target structure 5.

FIG. 1, step d, shows a tubular plunger 25 having an inner bore surrounding wire 17. The plunger moves from the upper proximal opening 13 of channel 11 towards distal opening 15 thus forcing the melted material 23 surrounding wire 17 from opening 15.

Finally, in step (e), the heating wire 17 and the plunger 25 are withdrawn from the pin for completing its implantation. Optionally, the extended channel 11 may be closed and stabilized by introducing a matching piece therein (not shown).

Figure 2:
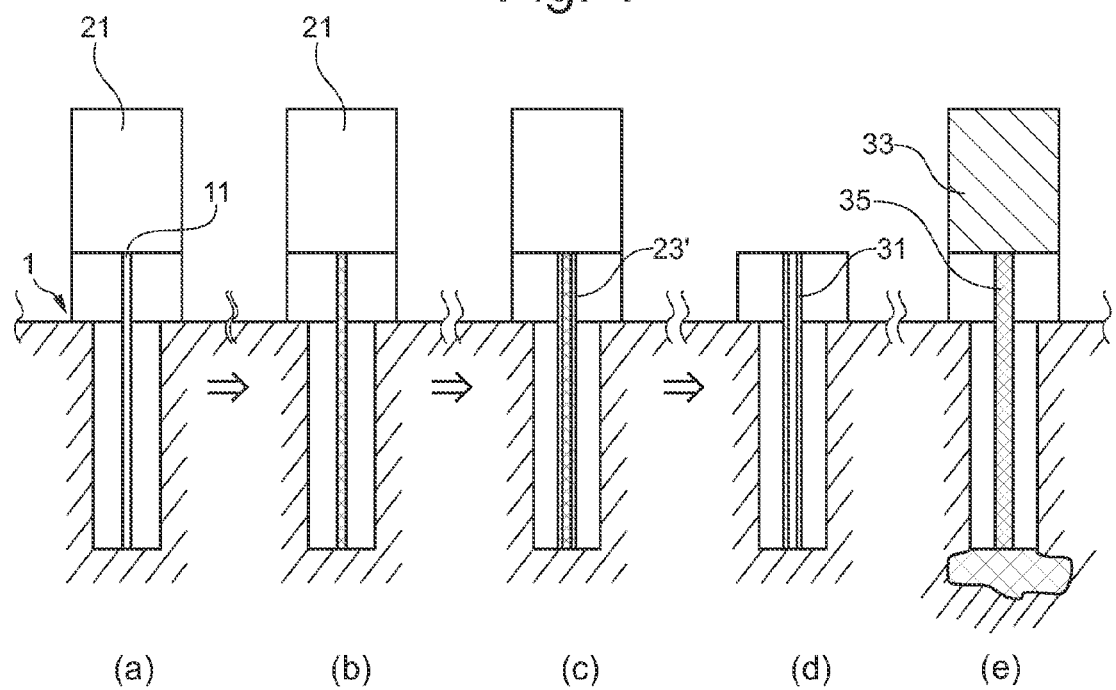
FIG. 2 shows an implantation pin kit and a sequence of its use during an implantation method according to a second embodiment of the present application.

In FIG. 2, an alternative sequence of a method for implanting an implantation pin 1 according to an embodiment of the present invention is schematically shown in its sequence steps.

Step (a) to (c) correspond to the respective steps described above with respect to FIG. 1 with the exception, that in this case, the material 23' in a region 31 adjacent to the heating wire 17 is not necessarily heated to an extent that it completely melts. Instead, this region 31 may only be preheated to an extent such that subsequently introduced melted material does not resolidify before reaching the distal opening 15.

In step (d), the implanting device 21 together with the heating wire 17 is removed.

Then, in step (e), a melted material supply device 33 is connected to the implantation pin's head 7. Liquefied melted material 35 can be introduced and pressed towards the distal opening 15. As the channel 11 has been previously heated, the additionally introduced melted material does not cool down and solidify but, instead, may even further heat the adjacent material 23' of the pin to a temperature at which it then melts such that the total amount of melted material may be even increased. The melted material 35 is then pushed out of the distal opening 15 and flows into pores of adjacent bone material, thereby augmenting the pin 1.

Figure 3:
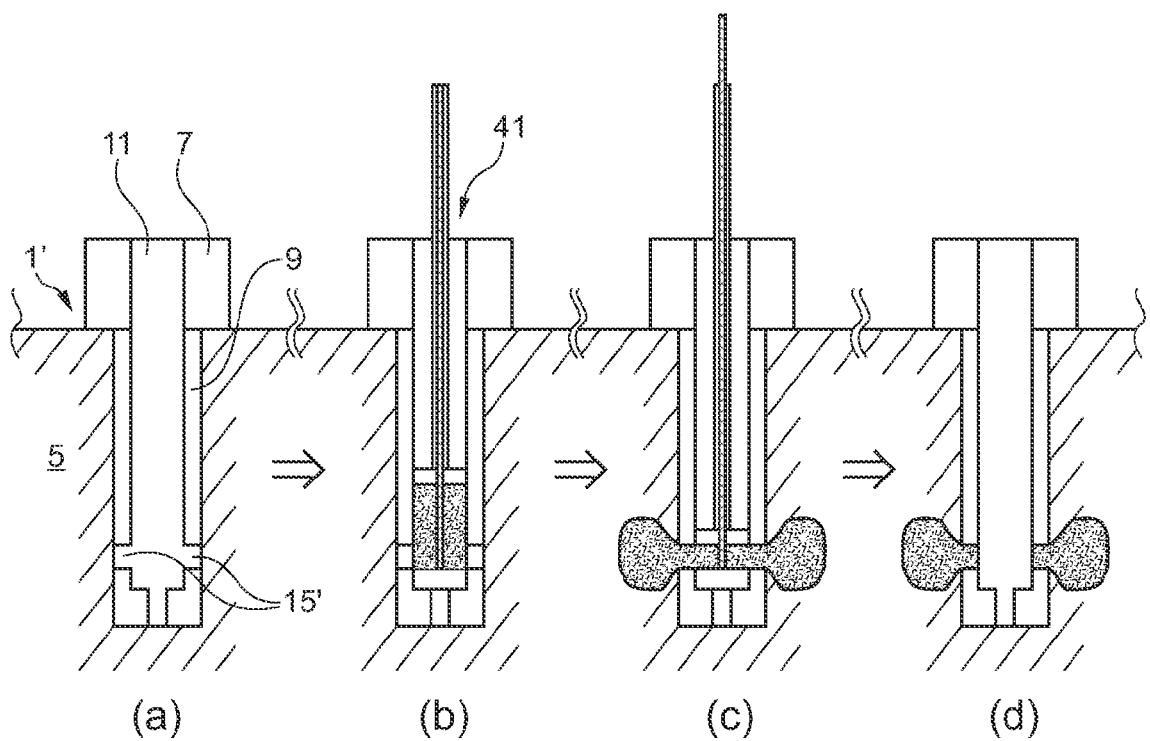
FIG. 3 shows an implantation pin kit and a sequence of its use during an implantation method according to a third embodiment of the present application.

In FIG. 3, a further alternative sequence of a method for implanting an implantation pin 1 according to an alternative embodiment of the present invention is schematically shown.

A modified implantation pin 1' is provided with additional distal opening 15' at lateral surfaces of the pin 1'. After introducing the implantation pin 1' into a recess in a target structure 5 (step (a)), an insert 41 is slidably introduced into the channel 9' of the pin 1' down to a position adjacent to the distal openings 15' (step (b)).

Figure 4:
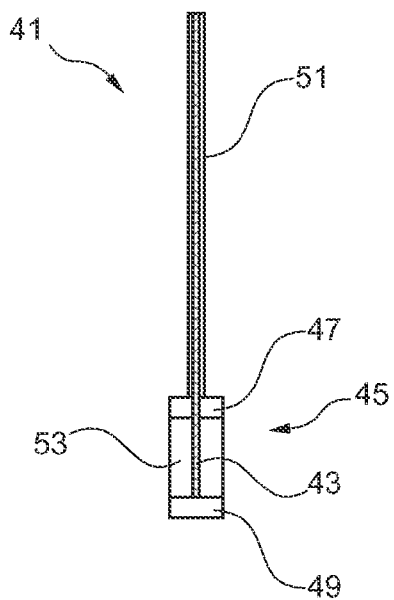
FIG. 4 shows an insert to be used in the implantation pin kit of FIG. 3

For better illustration, the insert 41 is separately shown in FIG. 4. The insert 41 comprises a heating wire 43 and a compression arrangement 45. The compression arrangement 45 has an upper compression plate 47 and a lower compression plate 49. Between the compression plates 47, 49, meltable material 53 is interposed. The upper compression plate is connected to a pushing rod 51 by means of which the upper compression plate 47 may be pushed towards the lower compression plate 49. The geometry of the entire insert 41 is adapted such that it can be introduced into the channel 11' of the pin 1'.

In step (c), electrical energy is applied to the heating wire 43 of the insert 41. As soon as the meltable material 53 interposed within the insert 41 melts, the pushing rod 51 which has been previously used to bring the entire insert 41 to its final position can then be used to push the upper compression plate 47 towards the lower compression plate 49. Thereby, the melted material 53 interposed between the compression plates 47, 49 is squeezed out and pushed towards and out of the distal openings 15'. There, it can finally augment and fix the pin 1' in the target structure 5.

Finally, the insert 41 can be removed (step (d)). Optionally, the remaining hollow channel 11' may be closed and stabilized by introducing a matching piece (not shown).

It should be noted that the terms "comprising" or "including" do not exclude other elements or steps and the "a" or "an" does not exclude a plurality. Also elements described in association with different embodiments and aspects may be combined. It should also be noted that reference signs in the claims shall not be construed as limiting the scope of the claims.

The invention claimed is:

1. An implantation pin kit comprising:
   a cannulated thermoplastic implantation pin having an axially extending channel with a proximal and distal end;
   an electric heating wire having a first end connected to a power source and a free second end, at least a portion of which including the free second end is adapted to be accommodated within at least a portion of the channel;
   wherein the channel of the pin extends along a longitudinal axis of the pin and connects a proximal opening at the proximal end of the pin with a distal opening at a distal end of the pin;
   wherein the electric heating wire free end is located adjacent the distal opening of the channel and an electric current passes through the wire to thermally heat and melt thermoplastic material surrounding the electric heating wire when received in the channel of the pin and;
   a hollow plunger mounted at the proximal opening at the proximal end of the channel with the wire received in the channel proximal end and surrounding the heating wire, wherein the plunger is adapted to move relative to the electric heating wire so as to press the melted thermoplastic material surrounding the heating wire in the channel along the electric heating wire and towards and out of the distal opening at the distal end of the pin to thereby fix the pin in neighboring tissue.

2. The implantation pin kit of claim 1,
wherein thermoplastic material of the pin adjacent to the channel is adapted to be thermally melted;
wherein the heating device is adapted to thermally heat material of the pin adjacent to the channel in order to melt it.

3. A implantation pin kit comprising:
a cannulated implantation pin having an axially extending channel, the implantation pin comprising a meltable material, the channel having an open proximal end and an open distal end;
an insert comprising an electrical heating wire and a meltable thermoplastic material surrounding the electrical heating wire, at least a portion of the insert is adapted to be accommodated in at least a portion of the channel adjacent the open distal end, the heating wire having a first end coupled to the power source and a second free end;
wherein the channel of the implantation pin extends along a longitudinal axis of the implantation pin and connects the proximal opening at a proximal end of the pin with the distal opening at a distal end of the pin;
wherein the electrical heating wire of the insert is adapted to allow electric current to pass through the wire to increase its temperature to thermally heat and melt the meltable thermoplastic material of the insert when the insert is located in the channel of the pin and;
a hollow plunger surrounding the heating wire mounted at the open proximal end of the channel, wherein the plunger is adapted to move along the longitudinal axis relative to the electrical heating wire so as to press the melted material of the insert in the cannulated implantation pin along the heating wire and towards and out of the distal opening at the distal end of the pin to thereby fix the pin in neighboring tissue.

4. An implantation pin kit comprising:
a cannulated implantation pin made of a meltable thermoplastic material having an axially extending channel therethrough, the channel having open proximal and an open distal end;
an insert surrounding an electrical heating wire, the electric heating wire having a first end connected to a power source and a second free end, the insert and wire received by the channel which electric wire comes into close mechanical contact with a portion of the insert comprising a thermoplastic material and the electric heating wire capable of melting the thermoplastic material of the insert;
wherein the channel of the pin extends along a longitudinal axis of the pin and connects the opening at the proximal end of the pin with the opening at a distal end of the pin, the free end of the electric heating wire located adjacent the opening at the distal end of the channel;
wherein the electrical heating wire is adapted to allow an electric current to pass through the wire to thermally heat and melt material of the insert when located in the channel of the pin and;
a plunger mounted at the proximal end of the cannulated implantation pin, wherein the plunger is adapted to surround and move toward the distal end of the channel relative to the electrical heating wire after the electrical heating wire melts the insert material so as to press the melted insert material in the cannulated implantation pin along the electrical heating wire and towards and out of the distal opening at the distal end of the pin to thereby fix the pin in neighboring tissue.

\* \* \* \* \*